United States Patent
Koernle

(10) Patent No.: US 9,518,939 B2
(45) Date of Patent: Dec. 13, 2016

(54) RADIOMETRIC DENSITY PROFILE MEASURING ARRANGEMENT

(71) Applicant: VEGA GRIESHABER KG, Wolfach (DE)

(72) Inventor: Ralf Koernle, Zell a.H. (DE)

(73) Assignee: Vega Grieshaber KG, Wolfach (DE)

( * ) Notice: Subject to any disclaimer, the term of this patent is extended or adjusted under 35 U.S.C. 154(b) by 106 days.

(21) Appl. No.: 14/563,125

(22) Filed: Dec. 8, 2014

(65) Prior Publication Data

US 2015/0168317 A1 Jun. 18, 2015

(30) Foreign Application Priority Data

Dec. 10, 2013 (DE) .................... 10 2013 225 509

(51) Int. Cl.
| | | |
|---|---|---|
| *G01N 23/10* | (2006.01) | |
| *G01T 1/20* | (2006.01) | |
| *G01N 9/24* | (2006.01) | |
| *G01F 23/288* | (2006.01) | |

(52) U.S. Cl.
CPC .......... *G01N 23/10* (2013.01); *G01F 23/2885* (2013.01); *G01N 9/24* (2013.01); *G01T 1/2006* (2013.01)

(58) Field of Classification Search
CPC .... G01F 23/2885; G01F 23/288; G01N 23/10; G01N 9/24; G01N 9/36; G01T 1/2006
See application file for complete search history.

(56) References Cited

U.S. PATENT DOCUMENTS

| | | | | |
|---|---|---|---|---|
| 2004/0025569 A1* | 2/2004 | Damm | .................. | G01F 23/288 73/32 R |
| 2011/0044427 A1* | 2/2011 | Featonby | .............. | G01F 23/288 378/52 |

FOREIGN PATENT DOCUMENTS

| | | |
|---|---|---|
| DE | 31 09 153 A1 | 3/1982 |
| DE | 197 22 837 A1 | 12/1998 |
| DE | 200 22 502 U1 | 11/2001 |
| DE | 101 27 224 A1 | 12/2002 |
| DE | 10 2011 085 943 A1 | 5/2013 |
| DE | 10 2011 085943 A1 | 5/2013 |
| DE | 10 2012 102 777 A1 | 10/2013 |
| EP | 1 239 303 A1 | 9/2002 |
| GB | 2326232 A * 12/1998 | ........... G01F 23/288 |
| WO | WO 99/17085 A1 | 4/1999 |
| WO | WO 02/01883 A2 | 3/2002 |

OTHER PUBLICATIONS

European Search Report from corresponding European Patent Application 14196907.1 dated Apr. 14, 2015.
(Continued)

*Primary Examiner* — Glen Kao
(74) *Attorney, Agent, or Firm* — Juneau & Mitchell

(57) ABSTRACT

A radiometric density profile measuring arrangement for determining a density profile of a bulk material located in a container comprising a multitude of radiation sources and a detection unit for detecting radioactive radiation with a scintillator to generate radiation-induced light flashes, a photosensitive element for generating an electrical signal based on said light flashes, and measuring electronics for processing the electrical signal, with the scintillator being embodied in an oblong fashion.

17 Claims, 3 Drawing Sheets

(56) References Cited

OTHER PUBLICATIONS

European Search Report from corresponding German Paten Application, dated Mar. 3, 2014.
European Search Report from corresponding European Patent Application 14196907.1 dated Jul. 13, 2015.
Office Action from corresponding German Patent Application, dated Sep. 9, 2014.

* cited by examiner

RADIOMETRIC DENSITY PROFILE MEASURING ARRANGEMENT

CROSS REFERENCE TO RELATED APPLICATIONS

This patent application claims priority to German Patent Application 10 2013 225 509.8, filed on Dec. 10, 2013.

STATEMENT REGARDING FEDERALLY SPONSORED RESEARCH OR DEVELOPMENT

No federal government funds were used in researching or developing this invention.

NAMES OF PARTIES TO A JOINT RESEARCH AGREEMENT

Not applicable.

SEQUENCE LISTING INCLUDED AND INCORPORATED BY REFERENCE HEREIN

Not applicable.

BACKGROUND

Field of the Invention

The present invention relates to a radiometric density profile measuring arrangement as well as a method for the radiometric detection of a density profile.

Background of the Invention

Various radiometric measuring arrangements are known from prior art for determining density profiles. These measuring arrangements are used in order to detect in a touchless fashion the distribution of layers of various bulk materials, for example in a container or a tank, characterized in their density.

An exemplary application for this method is the detection of different layers used in oil production. In oil production, for example sand, water, and crude oil are produced and collected in a tank, with the sand sedimenting, and crude oil and water separating in layers. For the further processing it is necessary to isolate the layers from each other and to separate sand and water from the crude oil, which can occur for example by draining some content of the tank in a lower section of said tank. In this method it is crucial to drain only water and sand, to the extent possible, and this way prevent wasting any crude oil.

Due to the fact that the materials given here differ in their density, appropriate density measuring arrangements and methods are applied.

The radiometric density measurement is here particularly characterized in that a measurement is possible independent from process conditions inside the tank and independent from the concrete chemical composition of the bulk materials to be measured. In particular, any potentially corrosive features are irrelevant, because the necessary measuring devices can be arranged outside the tank.

The underlying measuring principle utilizes the density-dependent absorption of gamma quanta in various media. For this purpose, gamma quanta are emitted from one or more radiation sources by the measuring device in the direction towards the bulk materials to be measured in order to detect the radiation intensity arriving there. Depending on the density of the bulk material located between the radiation source and the measuring device, more or less gamma quanta are absorbed by the bulk material, so that the radiation intensity at the location of the measuring device represents an indicator for the density of the bulk material.

Here, a detection of the radiation intensity usually occurs with the help of a so-called scintillation counter, which essentially comprises a scintillator for converting the gamma radiation into light pulses and a downstream arranged photomultiplier for generating electric impulses from said light pulses. The electric impulses are further processed, for example amplified and counted in measuring electronics arranged downstream. The number of the detected pulses is representative for the radiation intensity and thus also for the density of the bulk material. The fewer pulses are detected the higher the density of the bulk material.

In the methods of prior art, in a lower section of the tank the density is monitored in the area of a minimum fill level, which may not be fallen short of by the separating layer between water and crude oil, using a single measuring device. In the event that for example additionally a maximum fill level shall be monitored, for example for the water or the sand, here accordingly additional measuring devices are necessary, which are arranged at the respective fill levels.

In order to detect the composition of a multi-layered arrangement comprising bulk materials or to detect a density profile, many more measuring devices must be provided.

A respective arrangement is illustrated in FIG. 5.

FIG. 5 shows a radiometric density profile measuring arrangement 1 according to prior art, in which inside a tank 100 a multitude, in the present case six, radioactive radiation sources 3 are arrangement. The radiation sources 3 are arranged in a lance 4 and aligned such that their radiation cones 31 define a vertical radiation level, in which a number of detection units and/or measuring devices 5 is arranged, corresponding to the number of radiation sources 3. As discernible from FIG. 5, corresponding to the six radiation sources 3 provided, horizontally offset six vertically distributed measuring devices 5 are arranged according to the radiation sources 3.

By a horizontal arrangement of a measuring device 5 in reference to a radiation source 3 a density measurement can occur respectively at a fill level h and this way a density profile of the bulk material 99 located in the tank can be detected.

In another method known from prior art, respectively one radiation source and one measuring device allocated to said radiation source is moved vertically along or within the bulk material, and this way a density profile is detected.

The objective of the present invention is to simplify the detection of the density profile.

This objective is attained in a radiometric density profile measuring arrangement with the features of claim 1 and a measuring method for the radiometric detection of a density profile according to claim 13. Advantageous further developments are the objective of the dependent claims.

BRIEF SUMMARY OF THE INVENTION

In a preferred embodiment, a radiometric density profile measuring arrangement for determining a density profile of a bulk material located in a container comprising at least one radiation source and a detection unit for detecting radioactive radiation with a scintillator to generate radiation-induced light flashes, a photosensitive element for generating an electric signal based on said light flashes, and measuring electronics for processing an electric signal, wherein the scintillator is embodied in an oblong fashion.

In another preferred embodiment, the radiometric density profile measuring arrangement as described herein, wherein at least two radiations sources are allocated to the scintillator.

In another preferred embodiment, the radiometric density profile measuring arrangement as described herein, wherein between 2 to 10 radiation sources, preferably between 4 to 6 radiation sources, are allocated to the scintillator.

In another preferred embodiment, the radiometric density profile measuring arrangement as described herein, wherein the scintillator is embodied as an oblong, flexible cylinder.

In another preferred embodiment, the radiometric density profile measuring arrangement as described herein, wherein the radiation sources are arranged in one level with the scintillator.

In another preferred embodiment, the radiometric density profile measuring arrangement as described herein, wherein the measuring electronics comprises an amplitude measuring device.

In another preferred embodiment, the radiometric density profile measuring arrangement as described herein, wherein measuring electronics comprise a device for determining an amplitude distribution.

In another preferred embodiment, the radiometric density profile measuring arrangement as described herein, wherein the scintillator shows a length from 1 m to 10 m, preferably from 2 m to 8 m.

In another preferred embodiment, the radiometric density profile measuring arrangement as described herein, wherein the scintillator comprises an organic polymer, preferably polystyrene.

In another preferred embodiment, the radiometric density profile measuring arrangement as described herein, wherein the radiation sources and the scintillator are arranged in one level with a direction towards an expected change in density.

In another preferred embodiment, the radiometric density profile measuring arrangement as described herein, wherein the radiation sources are arranged and embodied such that the radiation cones of the radiation sources are not overlapping each other.

In another preferred embodiment, the radiometric density profile measuring arrangement as described herein, wherein the radiation sources show an angle of emission such that the radiation cone of a radiation source shows at the location of the scintillator a diameter in the longitudinal direction of the scintillator between 4 to 40 cm.

In another preferred embodiment, the radiometric density profile measuring arrangement as described herein, wherein the radiation sources show an angle of emission between 5° to 40°.

In another preferred embodiment, the radiometric density profile measuring arrangement as described herein, wherein an amplitude distribution of detected electric signals is detected and based on the amplitude distribution conclusions are drawn regarding a density profile of the bulk material.

In another preferred embodiment, the radiometric density profile measuring arrangement as described herein, wherein a statistical correction is performed of the amplitude distribution.

In another preferred embodiment, the radiometric density profile measuring arrangement as described herein, wherein the amplitude distribution is compared to reference amplitude distributions and based on this comparison conclusions are drawn regarding a density profile.

A method of use of a radiometric measuring arrangement with at least one radiation source and a detection unit for detecting radioactive radiation with a scintillator for generating light flashes, induced by radiation, a photosensitive element for generating an electrical signal based on the light flashes, and measuring electronics for processing the electric signal, wherein the scintillator is embodied in an oblong fashion.

DETAILED DESCRIPTION OF THE INVENTION

Figure 1:
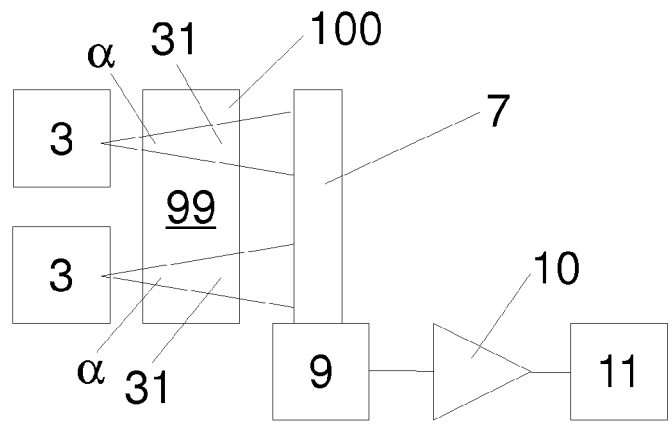
FIG. 1 is a line drawing evidencing a simplified block diagram of a radiometric density profile measuring arrangement according to the present application.

A radiometric density profile measuring arrangement according to the invention for the detection of a density profile of a bulk material located in a container comprises at least one radiation source and one detection unit for detecting radioactive radiation with a scintillator for generating radiation-induced light flashes, a photosensitive element for generating an electric signal based on the light flashes, and measuring electronics for processing the electric signal, with the scintillator being embodied in an oblong fashion and preferably arranged in the direction towards an expected density change. Several—particularly at least two—radiation sources may be allocated to the scintillator, also preferably arranged offset in reference to each other in the direction of the expected density change.

In common measuring scenarios, in which for example the density profile of a bulk material present in the tank is detected, the direction of the expected density change will usually be the vertical direction. However, other applications are also possible, in which a density change occurs, for example based on a processing in the horizontal direction or an arbitrary other direction.

A measuring arrangement according to the invention allows the detection of a density profile of the bulk material located in a container with the help of a single measuring device. Here, the recognition that the light flashes generated in the oblong scintillator are subject to a damping during their distribution in the scintillator is critical. While the number of the light flashes is representative for the density of the bulk material, conclusions can be drawn based on their intensity for a location of origin within the scintillator and thus, e.g., for an allocated fill level.

For the detection of a density profile as finely defined as necessary, for example 2 to 10 radiation sources may be allocated to the scintillator. A subdivision can be yielded, sufficient for many applications, when 4 to 6 radiation sources are allocated to the scintillator.

As already described, the radiation sources are preferably arranged along the direction of an expected density change, particularly distributed vertically, for example according to the fill levels in which density information is required.

An arrangement which can be adjusted for many applications and used in many cases is yielded when the scintillator shows the form of an oblong, flexible cylinder. This way the scintilla-tor can be adjusted to various container forms and arranged in a space-saving fashion.

An arrangement beneficial for measurement can be achieved when the radiation sources are arranged in one level with the scintillator.

A detection of the density profile can occur, for example, by evaluating the electric signal detected in the measuring electronics with regards to the amplitudes of the individual pulses developing. For this purpose, the measuring electronics comprise preferably an amplitude measuring device, which is capable of detecting the maximum amplitude of the individual pulses. Preferably the amplitude measuring device is embodied such that the amplitude progression of the individual pulses is detected.

The detection of the density distribution can occur via a device to detect an amplitude distribution, whereby the density distribution may occur, for example, by a comparison of the detected amplitude distribution with reference amplitude distributions.

In order to allow implementing such a comparison, it is beneficial for the measuring electronics to show memory for saving the reference amplitude distributions and/or the detected amplitude distribution. A comparison may occur for example via a comparison device.

A respective comparison may also occur, which is not excluded in the present invention, in a measuring computer allocated to the measuring arrangement, which commonly shows a higher computing capacity in order to perform the necessary comparing operations and corrections of potentially necessary measurements.

With presently available scintillator materials, scintillator lengths are possible up to 10 m. Longer scintillators cannot be used at this time due to the high damping affecting the light pulses in the available scintillator materials, because the light pulses developing at the free end of the scintillator could no longer be detected in the measuring electronics due to said damping.

Preferred lengths therefore range from 1 m to 10 m, with lengths between 2 m and 8 m also being possible.

In the present invention organic polymers are used as preferred scintillator materials, preferably polystyrene in the form of fibers with a diameter of 2 mm, because compared with other available materials they show good scintillation and light conducting features as well as good adaptability, for example to different shapes of containers.

The radiation sources and the scintillator are preferably arranged in one level with a direction of an expected change of density. The radiation sources are here preferably embodied such that they show their primary direction of emission in the direction of the scintillator and perpendicular in reference to the direction of the expected density change. Here, the primary direction of emission shall be understood as the axis of symmetry of a radiation cone generated by a radiation source.

This way, for example in case of an expected change of density in the vertical direction, by a horizontal alignment of the primary direction of emission of the radiation sources a good detection of a density profile can be yielded.

The radiation sources are here preferably arranged and embodied such that the radiation cones of the radiation sources are not overlapping each other. This way an allocation of sections on the scintillator to individual radiation sources can be achieved, which in turn facilitates the detection of the density profile.

However, this does not exclude the radiation cones of individual emitters overlapping each other.

By a greater pulse rate achieved by overlapping radiation cones the measurement can occur more precisely and/or faster using the same emitter. Or, some radiation sources may be omit-ted. The radiation angles may even be expanded such that every emitter reaches the scintillator in its entire expansion.

The radiation sources preferably show an angle of emission such that the radiation cone of a radiation source shows at the location of the scintillator a diameter from 4 cm to 40 cm in the longitudinal direction of the scintillator. This way sufficient allocation can be achieved to a measuring height within which a density detection occurs. Typically, the radiation sources used show an angle of emission from 5° to 40°. In a typical distance of 50 cm between the radiation source and the scintillator, it can be achieved that through one radiation source a layer with a density of approximately 2 cm to 16 cm is used for the detection of density.

A typical measuring method for the radiometric detection of a density profile is preferably performed with a measuring arrangement as described above, with an amplitude distribution of detected electric signals being detected, and based on said amplitude distribution conclusions are drawn for a density profile of the bulk material. As already explained, in radiometric measuring methods typically gamma quanta are emitted from a radiation source in the direction towards a scintillator, which converts the arriving gamma quanta into a number of light pulses corresponding to the intensity of the radiation. The light pulses are subsequently further processed in measuring electronics, with it being possible to detect the density profile underlying the measurement of bulk material arranged between the radiation sources and the scintilla-tor using the quantification of the arriving light pulses as well as an analysis these light pulses with regards to their amplitude and a distribution of these amplitudes.

Due to the fact that both the development of the light pulses within the scintillator, a damping effect acting upon the light pulses within the scintillator, as well as a conversion of the light pulses into electric signals, for example in a photomultiplier, represent processes subject to statistical fluctuations, they are preferably considered in the signal analysis. Preferably a statistical correction is performed of the amplitude distribution, with preferably the above-stated three factors being considered.

A particularly simple embodiment of the method can be achieved when the detected amplitude distribution is compared to reference amplitude distributions, and based on this comparison conclusions are drawn for a density profile.

According to the invention, a radiometric measuring arrangement is used with at least one radiation source and a detection unit for detecting radioactive radiation with a scintillator for generating radiation-induced light flashes, a photosensitive element for generating an electric signal based on the light flashes, and measuring electronics for processing the electric signals, with the scintillator being embodied in an oblong fashion, in order to detect a density profile of a bulk material located in a container.

DETAILED DESCRIPTION OF THE FIGURES

FIG. 1 shows a simplified block diagram of a radiometric density profile measuring arrangement 1 for determining a density profile of a bulk material 99 located in a container 100. As discernible from the illustration of FIG. 1, two radiation sources 3 are provided, which radiate through the container 100 with the bulk material 99 arranged therein in the direction towards a scintillator 7 embodied in an oblong fashion. The radiation sources 3 are embodied such that an angle of emission α of the radiation sources 3 is selected such that radiation cones 31 generated by the radiation sources are not overlapping each other upon reaching the scintillator 7.

A photosensitive element, embodied as a photomultiplier 9, is arranged downstream in reference to the scintillator 7, in which the light flashes generated based on the gamma quanta emitted by the radiation sources 3 are converted into electric signals. An amplifier 10 is ar-ranged downstream thereof for better processing these signals in the photomultiplier 9, which amplifies and filters the signals generated in the photomultiplier 9 and renders them available for further processing to measuring electronics 11, arranged downstream. Then, in the measuring electronics 11, a further processing of the generated electric signals can occur, and particularly an analysis of the detected electric impulses with regards to their amplitude and amplitude distribution.

Figure 2:
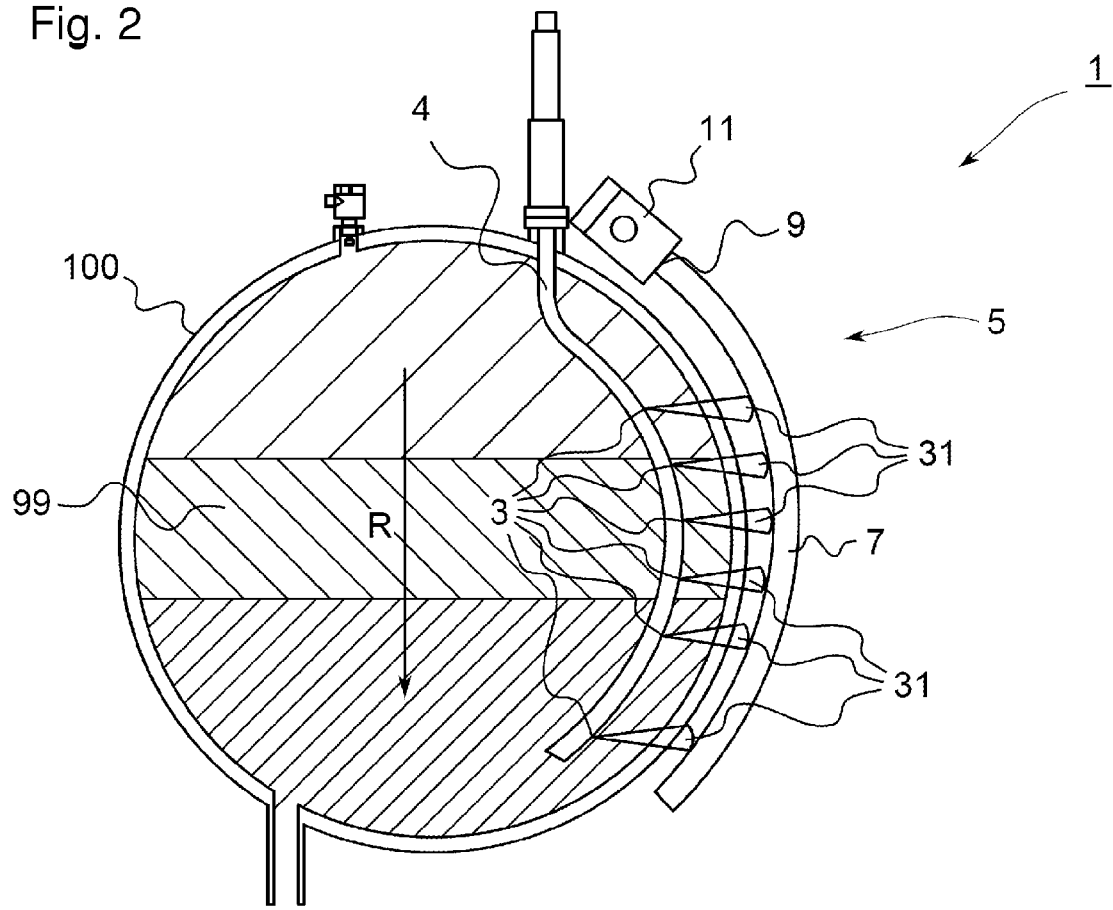
FIG. 2 is a line drawing evidencing an exemplary embodiment for a radiometric density profile measuring arrangement.

FIG. 2 shows a practical exemplary embodiment of the measuring arrangement 1 of FIG. 1.

In the measuring arrangement 1 in FIG. 2 the radiation sources 3 are arranged at a lance 4, which is arranged inside the tank 100 essentially extending parallel in reference to its exterior wall. In the container 100, which in the present exemplary embodiment is formed as a spherical tank, for example the products sand, water, and crude oil may be contained as bulk material 99, typically yielded when producing oil. The components mentioned above as examples will form a density profile in the spherical tank 100, with typically the sand dropping to the bottom of the tank 100, the water collecting thereabove, and the crude oil being located on top of the water layer. This way a direction R of an expected density change results, which in the present exemplary embodiment extents vertically. Accordingly, a change of the density in the vertical direction is particularly interesting for the respective measurement of the density profile. The radiation sources 3 are therefore arranged on the lance 4 such that they radiate essentially in the horizontal direction, i.e. perpendicular in reference to the direction R of an expected change of density. The radiation sources 3 are additionally embodied such that their primary direction of emission H is located in a vertically extending level, in which a scintillator 7 is also arranged, embodied in a tubular fashion.

In the present exemplary embodiment the tubular embodied scintillator 7 comprises an organic polymer which is coated with a light-impermeable layer and coupled at its ends with a photo-multiplier 9. As shown in the above-described block diagram, an amplifier 10 and measuring electronics 11 are arranged downstream in reference to the photomultiplier 9, with the amplifier 10 not being shown in the illustration in FIG. 2.

In the exemplary embodiment shown in FIG. 2, for example six radiation sources 3 are shown, with their radiation cones 31 essentially being arranged horizontally and particularly not from overlapping each other when reaching the scintillator 7, seen in the longitudinal direction L of the scintillator 7.

Figure 3:
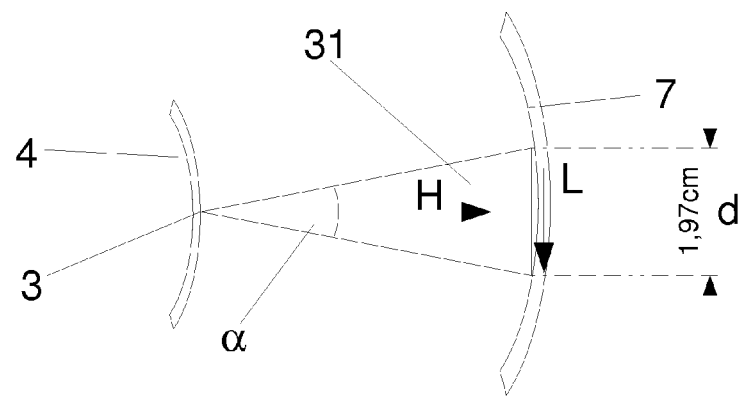
FIG. 3 is a line drawing evidencing an enlarged detail of FIG. 2.

FIG. 3 shows an enlarged detail of FIG. 2, in which a section of the lance 4 is shown with a radiation source 3 arranged thereon, with the opening angle α of the radiation cone 31 as well as the primary direction of emission H of the radiation source 3 being particularly clearly discernible in this view. Based on the opening angle α, when the gamma quanta emitted by the radiation source 3 impinges the scintillator 7, a diameter d develops in the longitudinal direction L of the scintillator 7. The longitudinal direction L of the scintillator 7 is essentially detected by its longitudinal axis, with curved forms also being possible, adjusted to the respective container 100, as shown in FIG. 2. In these cases the longitudinal direction L of the scintillator 7 to be analyzed represents the tangent in the level defined by the radiation sources to the scintillator 7 at the intersection of a scintillator surface with the primary direction of emission H of the radiation source 3 respectively analyzed.

Figure 4:
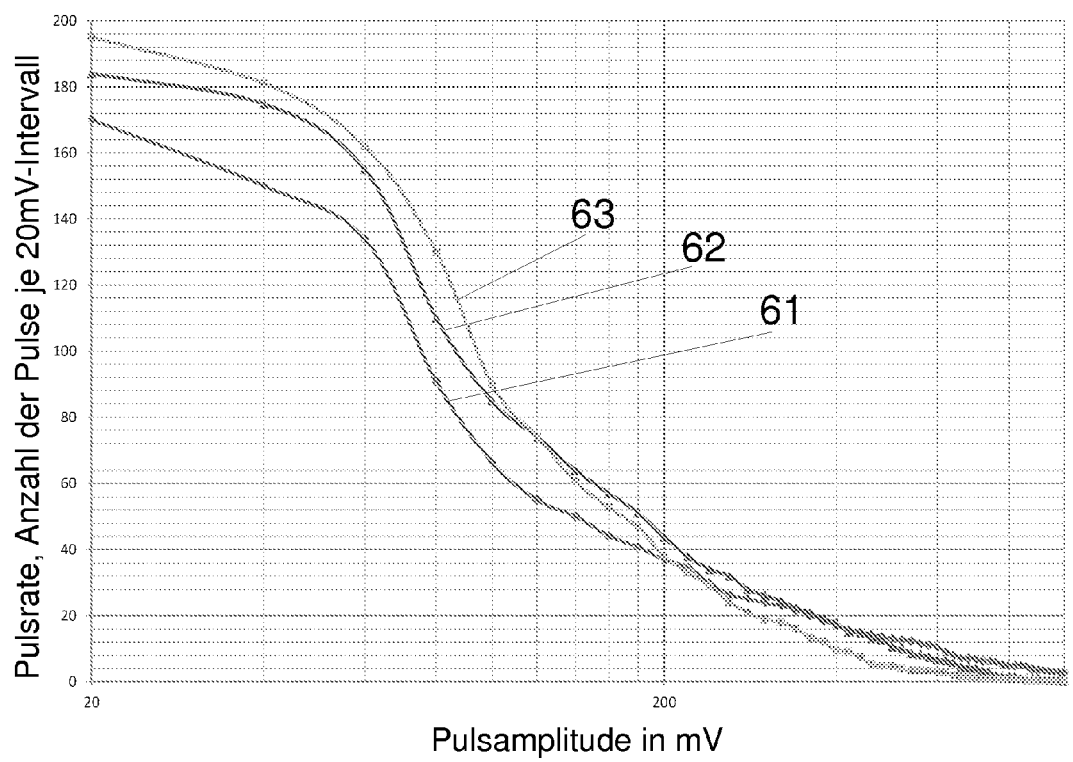
FIG. 4 is a line drawing evidencing representative amplitude distributions, which may be detected by a measuring arrangement according to FIGS. 1 and 2.
Figure 5:
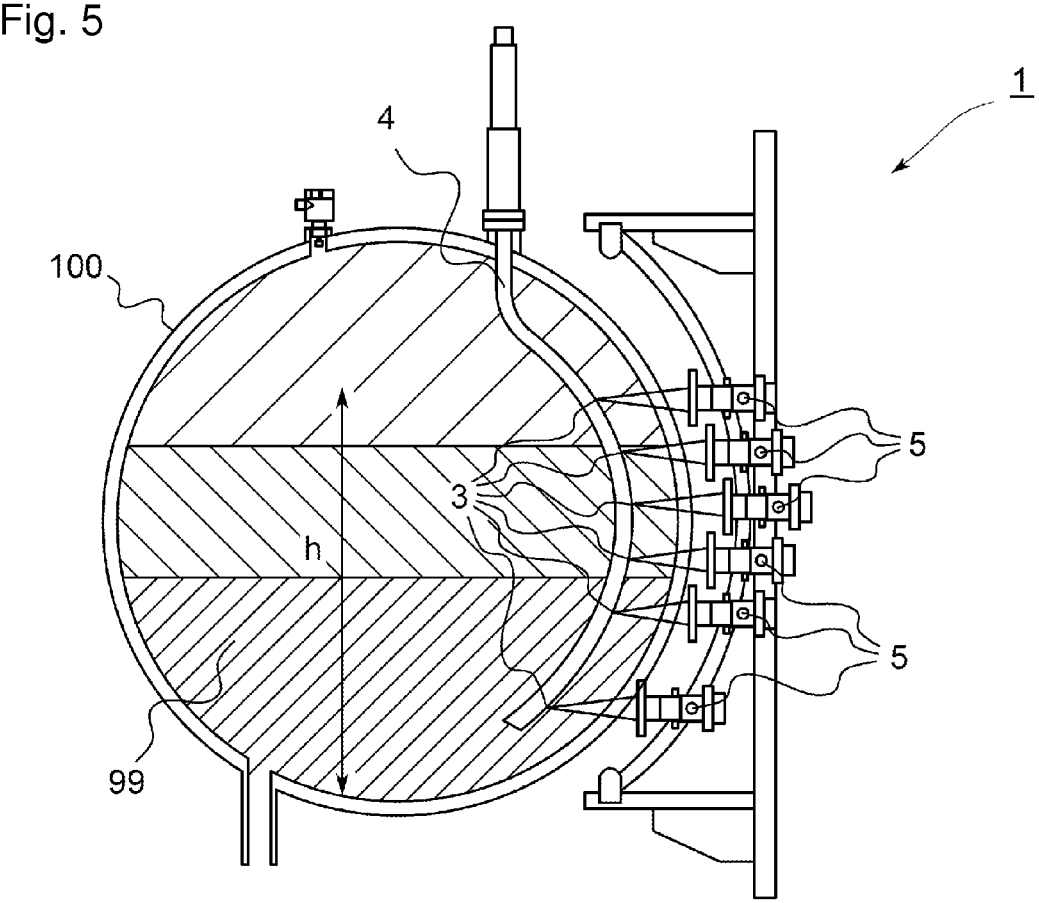
FIG. 5 is a line drawing evidencing a radiometric density profile measuring arrangement according to prior art (already discussed).

FIG. 4 shows three exemplary amplitude distributions of radiation sources 3, which irradiate different sections of the scintillator. These scintillator sections are located at a distance of 0 m (curve 61), 1 m (curve 62), and 3 m (curve 63) from the photomultiplier. However it is clearly discernible from FIG. 4 that for example the radiation source 3, which is arranged at a distance of 3 m from the photomultiplier 9, yields a lower number of pulses with high pulse amplitudes and thus a higher number of pulses with lower pulse amplitudes. The radiation source 3 arranged at a distance of 1 m from the photomultiplier 9 accordingly yields a slightly higher rate of electric pulses with a high rate (600 mV to 1000 mV) and in a moderate rate 200 mV to 500 mV, with accordingly the number of pulses with a low amplitude being lower than in case of a radiation source showing a distance of 3 m from the photomultiplier 9.

The third source arranged at a distance of 3 m therefore yields the lowest number of impulses compared to the other two sources, in a moderate and high amplitude range, here 250 mV to 1000 mV, with the number of impulses in the low amplitude range being the highest in the range from 0 mV to 100 mV.

Due to the fact that the above-stated sources generate at the respectively allocated point of the scintillator 7 an essentially identical number of pulses with an essentially identical intensity distribution, the present differences are caused almost exclusively by the damping effect acting upon the light pulses generated in the scintillator 7, so that conclusions can be drawn regarding the place of origin within the scintillator 7 based on the detected distribution of amplitudes. With this underlying knowledge, using appropriate mathematics and statistical methods or, as already described, using reference amplitude distributions, a density distribution inside the tank 100 can be concluded.

Here it is particularly advantageous when in general the potential bulk materials and their densities are known in advance, because this way certain reference scenarios can be assumed.

LIST OF REFERENCE NUMBERS

1 Measuring arrangement
3 Radiation source
4 Lance
5 Detection unit and/or measuring device
7 Scintillator
9 Photomultiplier/photosensitive element
10 Amplifier
11 Measuring electronics
13 Amplitude measuring device
31 Radiation cone
99 Bulk material
100 Container/tank
α Angle of emission
l Length
R Direction
d Diameter H Primary direction of emission
L Longitudinal direction
h Fill height The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable equivalents.

We claim:

1. A radiometric density profile measuring arrangement for determining a density profile of a bulk material located in a container comprising at least one gamma radiation source and a detection unit for detecting radioactive gamma radiation with a scintillator to generate gamma radiation-induced light flashes, a photosensitive element for generating an electric signal based on said light flashes, and measuring electronics for processing an electric signal, wherein the scintillator is elongated and the measuring electronics have an amplitude measuring device and a device to determine a distribution of amplitudes, consisting of a correlation between pulse amplitudes in mV and the number of pulses in each predetermined mV-interval, in order to suggest a density profile of the bulk material.

2. The radiometric density profile measuring arrangement of claim 1, wherein at least two gamma radiations sources are allocated to the scintillator.

3. The radiometric density profile measuring arrangement of claim 1, wherein between 2 to 10 gamma radiation sources, are allocated to the scintillator.

4. The radiometric density profile measuring arrangement of claim 1, wherein the scintillator is embodied as an oblong, flexible cylinder.

5. The radiometric density profile measuring arrangement of claim 1, wherein the gamma radiation sources are arranged in a plane with the scintillator.

6. The radiometric density profile measuring arrangement of claim 1, wherein the scintillator shows a length from 1 m to 10 m.

7. The radiometric density profile measuring arrangement of claim 1, wherein the scintillator comprises an organic polymer.

8. The radiometric density profile measuring arrangement of claim 1, wherein the gamma radiation sources and the scintillator are arranged in a plane with a direction towards an expected change in density.

9. The radiometric density profile measuring arrangement of claim 1, wherein the gamma radiation sources are arranged and embodied such that a radiation cone does not overlap the gamma radiation sources.

10. The radiometric density profile measuring arrangement of claim 9, wherein the gamma radiation sources show an angle of emission such that a radiation cone of a gamma radiation source shows at the location of the scintillator a diameter in the longitudinal direction of the scintillator between 4 to 40 cm.

11. The radiometric density profile measuring arrangement of claim 9, wherein the gamma radiation sources show an angle of emission between 5° to 40°.

12. The radiometric density profile measuring arrangement of claim 1, wherein an amplitude distribution of detected electric signals is detected and, based on the amplitude distribution, conclusions are drawn regarding a density profile of the bulk material.

13. The radiometric density profile measuring arrangement of claim 12, wherein a statistical correction is performed of the amplitude distribution.

14. The radiometric density profile measuring arrangement of claim 12, wherein the amplitude distribution is compared to reference amplitude distributions and, based on this comparison, conclusions are drawn regarding a density profile.

15. The radiometric density profile measuring arrangement of claim 1, wherein between 4 to 6 gamma radiation sources are allocated to the scintillator.

16. The radiometric density profile measuring arrangement of claim 1, wherein the scintillator shows a length from 2 m to 8 m.

17. The radiometric density profile measuring arrangement of claim 1, wherein the scintillator comprises polystyrene.

* * * * *